(12) United States Patent
Norstrem et al.

(10) Patent No.: US 12,138,210 B2
(45) Date of Patent: Nov. 12, 2024

(54) CERVICAL ORTHOTIC CUSHION AND TECHNIQUES

(71) Applicant: Core Products International, Inc., Osceola, WI (US)

(72) Inventors: Paul R. Norstrem, Amery, WI (US); Douglas W. Mattison, Forest Lake, MN (US)

(73) Assignee: Core Products International, Inc., Osceola, WI (US)

(*) Notice: Subject to any disclaimer, the term of this patent is extended or adjusted under 35 U.S.C. 154(b) by 1108 days.

(21) Appl. No.: 16/946,830

(22) Filed: Jul. 8, 2020

(65) Prior Publication Data

US 2021/0007924 A1  Jan. 14, 2021

Related U.S. Application Data

(60) Provisional application No. 62/871,987, filed on Jul. 9, 2019.

(51) Int. Cl.
*A61H 1/02* (2006.01)
*A61F 7/00* (2006.01)
(Continued)

(52) U.S. Cl.
CPC ............. *A61H 1/0296* (2013.01); *A61F 7/02* (2013.01); *A61H 1/008* (2013.01); *A61F 2007/0012* (2013.01); *A61F 2007/0219* (2013.01); *A61F 2007/0225* (2013.01); *A61F 2007/0242* (2013.01); *A61F 2007/0277* (2013.01);
(Continued)

(58) Field of Classification Search
CPC .................. A61H 1/0296; A61H 1/008; A61H 2201/0134; A61H 2201/0157; A61H 2201/1609; A61H 2203/0456; A61H 2201/0192; A61H 2201/1284; A61H 2205/04; A61F 2007/0012; A61F 2007/0219; A61F 2007/0225; A61F 2007/0242; A61F 2007/0277;
(Continued)

(56) References Cited

U.S. PATENT DOCUMENTS 2,835,905 A   5/1958  Helgi
3,648,308 A * 3/1972  Greenawalt .......... A47G 9/1081
                                                   5/636

(Continued)

OTHER PUBLICATIONS

"U.S. Appl. No. 14/488,876 Response filed Sep. 11, 2018 to Final Office Action mailed Jul. 11, 2018", 10 pgs.
(Continued)

*Primary Examiner* — Myles A Throop
(74) *Attorney, Agent, or Firm* — Schwegman Lundberg & Woessner, P.A.

(57) ABSTRACT

Techniques for a cervical orthotic device are provided. In an example, the device can include a base, sidewalls extending upwardly from the base, and a cervical support surface opposite the base and configured to unite the sidewalls. In certain examples, the sidewalls can include opposingly paired lateral sidewalls and first and second longitudinal sidewalls. In some examples, the cervical support surface can include a first planar portion adjacent the first longitudinal sidewall, a second planar portion adjacent the second longitudinal sidewall, and an arcuate portion intermediate the planar portions.

20 Claims, 6 Drawing Sheets

(51) Int. Cl.
   *A61F 7/02* (2006.01)
   *A61F 7/10* (2006.01)
   *A61H 1/00* (2006.01)
(52) U.S. Cl.
   CPC . *A61F 2007/0282* (2013.01); *A61F 2007/108* (2013.01); *A61H 2201/0134* (2013.01); *A61H 2201/0157* (2013.01); *A61H 2201/1609* (2013.01); *A61H 2203/0456* (2013.01)
(58) Field of Classification Search
   CPC ........ A61F 2007/0282; A61F 2007/108; A61F 2007/0288
   USPC ................................................ 5/636; D6/601
   See application file for complete search history.

(56) References Cited

U.S. PATENT DOCUMENTS

| | | | |
|---|---|---|---|
| 4,424,599 A * | 1/1984 | Hannouche | A47G 9/1081 5/636 |
| 4,679,263 A | 7/1987 | Honer | |
| D296,403 S * | 6/1988 | Palm | D6/601 |
| 4,754,513 A | 7/1988 | Rinz | |
| 4,777,678 A | 10/1988 | Moore | |
| 4,821,355 A | 4/1989 | Burkhardt | |
| 4,829,614 A * | 5/1989 | Harper | A47G 9/1081 5/636 |
| 4,916,765 A | 4/1990 | Castronovo, Jr. | |
| 5,279,310 A | 1/1994 | Hsien | |
| 5,423,099 A | 6/1995 | Gulli | |
| 5,481,771 A | 1/1996 | Burk, IV | |
| 5,584,086 A * | 12/1996 | VanWinkle | A61F 7/02 5/636 |
| 5,611,765 A | 3/1997 | Koch, Jr. | |
| 5,797,154 A * | 8/1998 | Contreras | A47G 9/1081 5/636 |
| 5,940,913 A * | 8/1999 | Horowitz | A47G 9/1081 5/636 |
| 6,292,964 B1 | 9/2001 | Rose et al. | |
| 6,345,401 B1 | 2/2002 | Frydman | |
| 6,381,784 B1 | 5/2002 | Davis et al. | |
| 6,471,726 B2 | 10/2002 | Wang | |
| 6,751,818 B2 * | 6/2004 | Troop | A61G 7/072 5/636 |
| 7,013,512 B1 | 3/2006 | Hsu | |
| 7,681,263 B1 * | 3/2010 | Hawkins | A47G 9/10 5/640 |
| D619,401 S * | 7/2010 | Deenadayalu | D6/601 |
| 8,713,732 B2 | 5/2014 | Dennewald | |
| D706,062 S * | 6/2014 | Murray | D6/601 |
| 9,186,004 B2 * | 11/2015 | Dennewald | A47G 9/1081 |
| 9,700,160 B2 | 7/2017 | Kim | |
| 10,188,575 B2 * | 1/2019 | Norstrem | A61H 1/0296 |
| 2005/0222651 A1 * | 10/2005 | Jung, Jr. | A61F 7/02 607/104 |
| 2013/0305458 A1 | 11/2013 | Kim | |
| 2014/0359944 A1 | 12/2014 | Thompson et al. | |
| 2015/0080949 A1 | 3/2015 | Norstrem | |
| 2019/0099289 A1 * | 4/2019 | Beck | A61J 13/00 |
| 2023/0148772 A1 * | 5/2023 | Boehlen | A47G 9/1081 5/636 |

OTHER PUBLICATIONS

"U.S. Appl. No. 14/488,876, Advisory Action mailed Aug. 29, 2017", 3 pgs.
"U.S. Appl. No. 14/488,876, Corrected Notice of Allowability mailed Nov. 8, 2018", 2 pgs.
"U.S. Appl. No. 14/488,876, Final Office Action mailed May 31, 2017", 14 pgs.
"U.S. Appl. No. 14/488,876, Final Office Action mailed Jul. 11, 2018", 13 pgs.
"U.S. Appl. No. 14/488,876, Non Final Office Action mailed Oct. 21, 2016", 14 pgs.
"U.S. Appl. No. 14/488,876, Non Final Office Action mailed Dec. 21, 2017", 11 pgs.
"U.S. Appl. No. 14/488,876, Notice of Allowance mailed Oct. 19, 2018", 5 pgs.
"U.S. Appl. No. 14/488,876, Response filed Feb. 21, 2017 to Non Final Office Action mailed Oct. 21, 2016", 10 pgs.
"U.S. Appl. No. 14/488,876, Response filed Jul. 31, 2017 to Final Office Action mailed May 31, 2017", 8 pgs.
"U.S. Appl. No. 14/488,876 Response filed Mar. 21, 2018 to Non-Final Office Action mailed Dec. 21, 2017.pdf", 9 pgs.
Harrison, Donald D., "Spinal Biomechanics, a Chiropractic Perspective", Journal of Clinical Chiropractic, 1992, (1992), 2 pgs.

* cited by examiner

CERVICAL ORTHOTIC CUSHION AND TECHNIQUES

CLAIM OF PRIORITY AND RELATED APPLICATIONS

This application claims the benefit of priority to Norstrem et al., Provisional Patent Application No. 61/871,987, filed on Jul. 9, 2019, titled, CERVICAL ORTHOTIC TECHNIQUES, which is hereby incorporated by reference herein in its entirety.

TECHNICAL FIELD

The disclosure herein relates generally to traction devices and more particularly to improved cervical orthotic techniques.

BACKGROUND

The human backbone, the vertebral column, provides a structure for skeletal support and consists of twenty-four articulating vertebrae and nine fused vertebrae, with individual vertebrae named according to region and position. The articulating vertebrae are, superior to inferior, the cervical (C1-C7), the thoracic (T1-T12), and the lumbar (L1-L5). The articulating vertebrae of the column are generally separated from each other by intervertebral discs which provide/impart a great deal of flexibility and resiliency for these column regions. The fused vertebrae, superior to inferior, include the sacral (S1-S5) and coccygeal (Co1-Co5).

The cervical vertebrae are the vertebrae immediately inferior to the skull. The first, topmost vertebrae (i.e., the atlas) along with the second vertebrae (i.e., the axis) delimit the joint connecting the skull and spine.

Via a cervical curve, convex forward and generally extending from the axis to the second thoracic vertebrae, the head is properly supported, with the cervical vertebrae allowing mobility of the head and cervical spine via flexion and extension of the cervical spinal structures. "Curves" are likewise associated with each of the thoracic (concave forward), lumbar (convex forward) and sacral (concave forward) regions of the vertebral column, with the thoracic and lumbar curves known as the kyphotic and lordotic curves respectively.

While especially configured for resiliency, misalignment or dysfunction of articulating vertebrae of the spinal column, i.e., subluxation, are a fact of life for a majority of the population at any given time. With regard to the cervical spine, trauma, chronic poor posture, arthritis and muscle tension/spasm are primary sources of neck subluxation. For example, prolonged, frequent sleep postures, such as prone or face down, are known to create too much rotation for too long (i.e., suboccipital subluxation), resulting in excessive torsion in the upper most portion of the cervical spine. Moreover, prolonged, frequent sitting is known to create too much flexion for too long (i.e., atlantoaxial subluxation), resulting in a lessened or reversed curve of the of the cervical spine and stress upon the atlas/axis joint. Individuals seeking relief from cervical spine subluxations and the like can benefit from more focused cervical engagement not provided by conventional pillows, cushions and other devices.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which.

DETAILED DESCRIPTION

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments.

Figure 1:
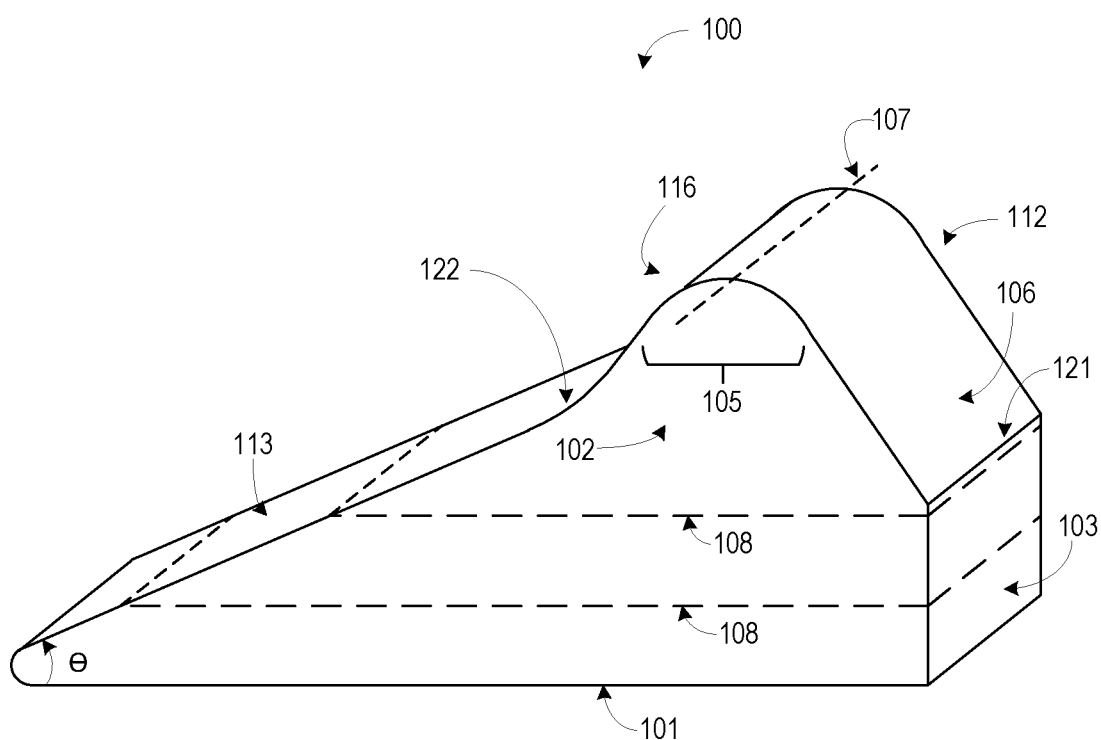
FIG. 1 is a perspective view of an improved cervical orthotic device.
Figure 2:
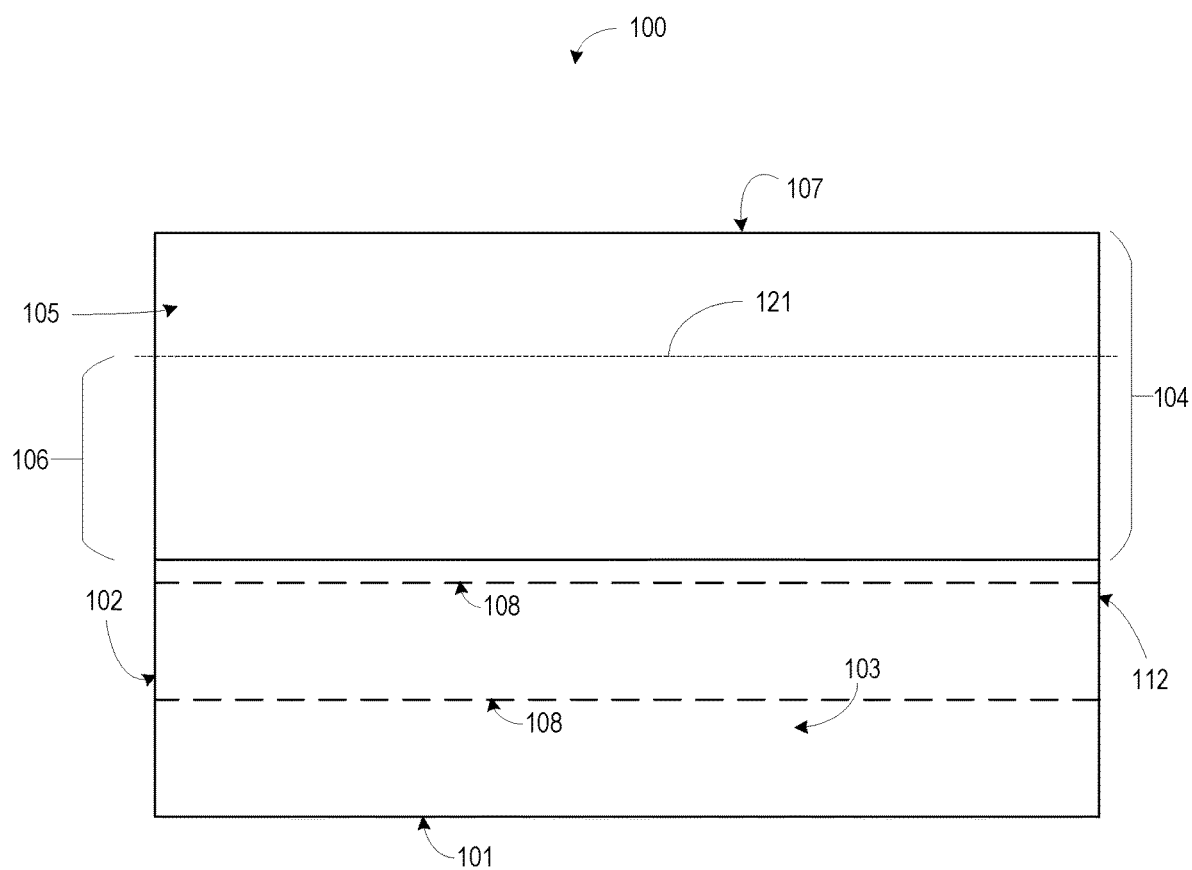
FIG. 2 is an elevation view of a minor side of the improved cervical orthotic device of FIG. 1.
Figure 3:
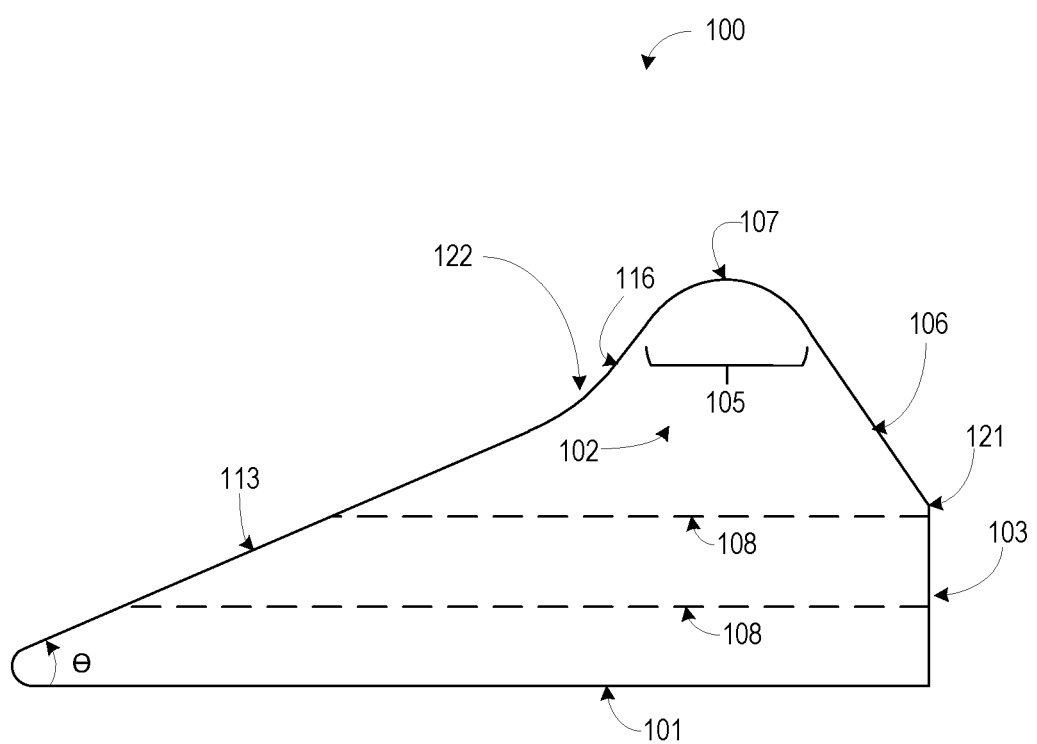
FIG. 3 is an elevation view of a major side of the improved cervical orthotic device of FIG. 1.

The present inventors have recognized techniques for an improved cervical orthotic device. The techniques can include inferior and superior passive cervical support, adjacent an actively engaged portion, or more particularly, passive supports characterized by "flats," i.e., planar segments or portions adjacent an engagement ridge line. In certain examples, an example cervical orthotic device can decrease pressure on soft tissue of the cervical spine and is readily adaptable to treat a range of patient cervical spine lengths. In certain examples, the techniques can initiate opening the anterior thoracic region for enhanced breathing during therapy. FIGS. 1-3 illustrate generally several views of an improved cervical orthotic device according to the present subject matter. FIG. 1 illustrates generally a perspective view of the example cervical orthotic device 100 according to the present subject matter. In certain examples, a cervical orthotic device 100 can include a base 101, opposingly-paired end walls (i.e., lateral sidewalls) 102, 112, opposingly-paired sidewalls (i.e., longitudinal sidewalls) 103, 113 and a cervical support surface. The cervical support surface can include an arcuate portion defining a cervical engagement ridge 105 intermediate first and second "flats," or more particularly, a first planar support portion 106 adjacent first longitudinal sidewall 103, and a second planar support portion 116 adjacent second longitudinal sidewall 113. Cervical engagement ridge 105 can be delimited by and/or correspond to an uppermost extremity, i.e., an apex 107, of the opposingly-paired lateral sidewalls 102, 112. In certain examples, a length of the first planar support portion 106 can be longer than a length of the second planar support portion 116.

In certain examples, the first longitudinal sidewall 103 can extend perpendicularly from the base 101 to meet the first planar cervical support portion 106 at a first node line 121. In certain examples, the second longitudinal sidewall 113 can extend from the base 101 at an acute angle (⊖) to meet the second planar cervical support portion 116 at a second node line 122. In certain examples, the acute angle (⊖) is less than 60°. In some examples, the acute angle (⊖) is less than 45°. In some examples, the acute angle (⊖) is less than 35°. In certain examples, the second longitudinal sidewall 113 can form a thoracic wedge and can provide support for a user's upper back while the apex 107 of the cervical orthotic device 100 engages the cervical spine of the user, such as a posterior portion of the cervical spine. In some examples, the thoracic wedge formed by the second longitudinal sidewall 113 can support at least a portion of thoracic spine of a user, but not the boney or muscular structure of the user's shoulders such as the shoulder blades. Such combination of support of the thoracic spine and lack of support of the user's shoulders can allow the user's shoulders to lower with respect to the thoracic spine. The lowering of the user's shoulders can allow for easier breathing during therapy of the cervical spine as the lowered shoulders naturally opens and relaxes the anterior portion of the user's chest. In certain examples, the perpendicular extension of the first longitudinal sidewall 103 from the base 101 is designed to not allow further engagement of the cervical orthotic device 100 with the back of the user's head. Such an arrangement allows for the weight of the user's head to assist with rotational cervical traction or the stretching of the cervical spine vertebra and muscles. In certain circumstances, such stretching of the anterior cervical spine may relieve pressure and pain in some users.

In certain examples, the base 101 can include a first major surface defining the bottom surface of the cervical orthotic device 100. The sidewalls, both longitudinal 103, 113 and lateral 102, 112 can extend from the first major surface of the base 101. In some examples, the base 101 can include multiple portions to allow the height of the apex 107 to be adjusted relative to a surface upon which the cervical neck orthotic device 100 is placed upon. In certain examples, one or more lower portions of the base 101 can be removed to lower the height of the apex 107, or one or more lower portions of the base 101 can be added to raise the height of the apex 107. In certain examples, where the base 101 includes multiple portions, each removable portion of the base 101 can include a first major surface and a second major surface, a portion of each lateral sidewall 102, 112 and a portion of each longitudinal sidewall 103, 113. In certain examples, the removable portions of the base 101 can include an attachment entity to allow secure attachment and easy removal of the removeable portions from the cervical neck orthotic device 100. Such attachment entities can include, but are not limited to, a portion of a zipper, a portion of a hook and loop device, a portion of a snap fastener, a portion of a button fastener, glue, adhesive tape, or combinations thereof. FIG. 1 illustrates generally lines 108 defined by at least one optional, separable portions of the base 101.

FIG. 2 illustrates generally an elevation view including the first longitudinal sidewall 103. The view can illustrate the locations of the apex 107, a portion of the cervical support surface 104 including the first planar cervical support surface 106 and a portion of the cervical engagement ridge 105, a first end wall or first lateral sidewall 102, and the second end wall or second lateral sidewall 112. FIG. 2 also shows lines 108 defined by optional, separable portions of the base 101.

FIG. 3 illustrates generally an elevation view of a major side of the cervical orthotic device 100 including the first lateral sidewall 102, or first end wall, of the cervical orthotic device 100. The view can illustrate the location of a first longitudinal sidewall 103, the second longitudinal sidewall 113, the planar cervical support portions 106, 116, the arcuate engagement surface or cervical engagement ridge 105 including the apex 107 and the base. FIG. 3 also shows lines 108 defined by and associated with optional removable portions of the base 101. In certain examples, the apex 107 can define a height of the cervical orthotic device as measured from a lower surface of the base 101 whether the base includes one or more removeable portions or not. In general, the height of the cervical orthotic device can range from about 2.5 inches (in.) to about be about 6 in. In some examples, each removeable portion of the base can vary between about 0.75 in. and 1.25 in.

In general, the line defined by where the first longitudinal sidewall 103 meets the lower surface of the base 101 can define a width of the cervical orthotic device 100. In certain examples, the width of the cervical orthotic device can range from about 3.5 in. to about 4.5 in. In some examples, a nominal width of the cervical orthotic device is about 4 in. In general, the line defined by where one of the lateral sidewalls 102, 112 meets the lower surface of the base 101 can define a length of the cervical orthotic device 100. In certain examples, the length of the cervical orthotic device 100 can range from about 6 in. to about 18 in. In certain examples, the length of the cervical orthotic device 100 can range from about 9 in. to about 12 in. In some examples, a nominal width of the cervical orthotic device is about 10.25 in.

Figure 4:
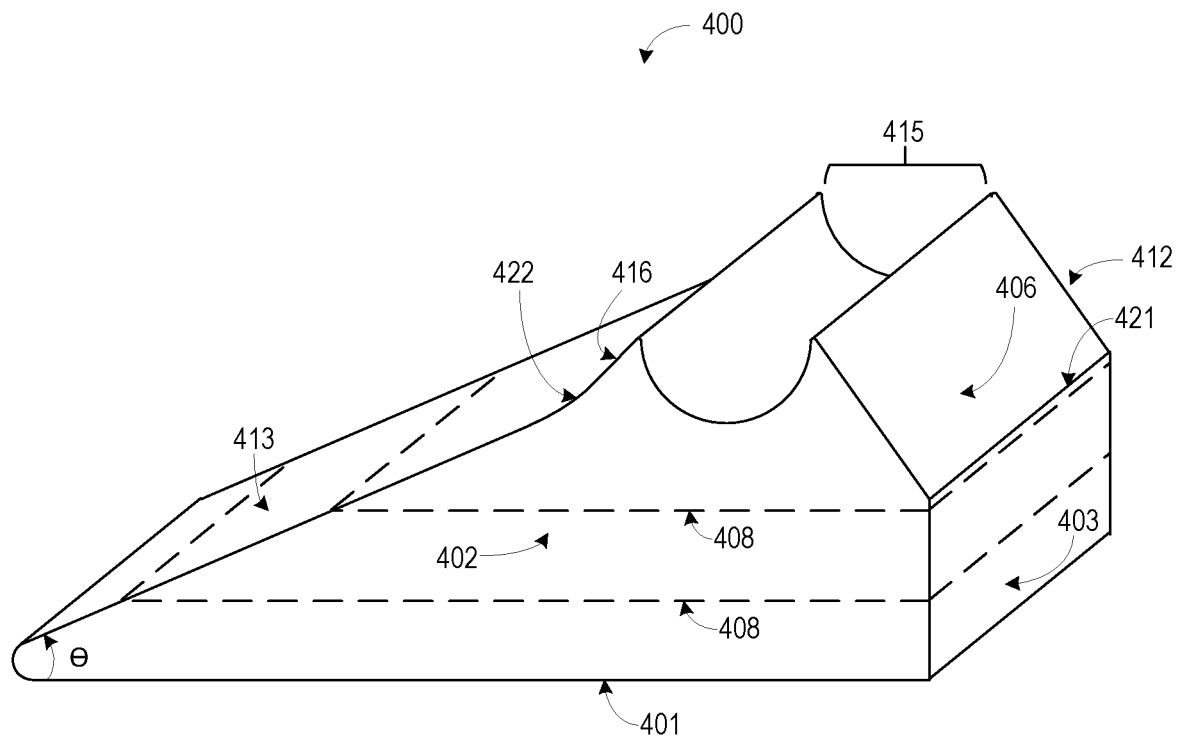
FIG. 4 is a perspective view of an improved cervical orthotic device.

FIG. 4 illustrates generally a perspective view of an example cervical orthotic device according to the present subject matter. In certain examples, a cervical orthotic device 400 can include a base 401, opposingly-paired end walls (i.e., lateral sidewalls) 402, 412, opposingly-paired sidewalls (i.e., longitudinal sidewalls) 403, 413 and a cervical support surface 104. The cervical support surface 404 can include a channel 415 intermediate first and second "flats," more particularly, a first planar cervical support portion 406 adjacent first longitudinal sidewall 403, and a second planar cervical support portion 416 adjacent second longitudinal sidewall 413. Sidewalls of the channel 415, channel sidewalls, can be delimited by and/or correspond to an uppermost extremity of the opposingly-paired lateral sidewalls 402, 412. In certain examples, the cervical orthotic device 400 can include an enhancement device (see FIG. 6; item 420) for placement in the channel 415. In some examples, the enhancement device, once placed in the channel 415, can form a cervical engagement ridge intermediate the first planar support portion 406 and the second planar support portion 416. In certain examples, a length of the first planar support portion 406 can be longer than a length of the second support surface 416. The example of FIG. 4 illustrates the channel as having a circular cross section, the present subject matter is not so limited. In some examples, the channel can include a rectangular, triangular, or squared-shaped 419 cross-section and a system can include an enhancement device (see FIG. 6; item 420) such as a cushion having a corresponding exterior shape to engage the channel and provide a cervical engagement ridge.

In certain examples, the first longitudinal sidewall 403 can extend perpendicularly from the base 401 to meet the first planar cervical support portion 406 at a first node line 421. In certain examples, the second longitudinal sidewall 413 can extend from the base 401 at an acute angle ($\ominus$) to meet the second planar cervical support portion 416 at a second node line 422. In certain examples, the acute angle ($\ominus$) is less than 60°. In some examples, the acute angle ($\ominus$) is less than 45°. In some examples, the acute angle ($\ominus$) is less than 35°. In certain examples, the second longitudinal sidewall 413 can form a thoracic wedge and can provide support for a user's upper back while an enhancement device of the cervical orthotic device 100 engages the cervical spine of the user. In some examples, the thoracic wedge formed by the second longitudinal sidewall 413 can support at least a portion of thoracic spine of a user, but not the boney or muscular structure of the user's shoulders such as the shoulder blades. Such combination of support of the thoracic spine and lack of support of the user's shoulders can allow the user's shoulders to lower with respect to the thoracic spine. The lowering of the user's shoulders can allow for easier breathing during therapy of the cervical spine as the lowered shoulders naturally opens and relaxes the anterior portion of the user's chest. In certain examples, the perpendicular extension of the first longitudinal sidewall 403 from the base 401 is designed to not allow further engagement of the cervical orthotic device 400 with the back of the user's head. Such an arrangement allows for the weight of the user's head to assist with rotational cervical traction or the stretching of the cervical spine vertebra and muscles. In certain circumstances, such stretching of the anterior cervical spine may relieve pressure and pain in some users.

In certain examples, the base 401 can include a first major surface defining the bottom surface of the cervical orthotic device 400. The sidewalls, both longitudinal and lateral can extend from the first major surface of the base 401. In some examples, the base 401 can include multiple portions to allow the height of the apex to be adjusted relative to a surface upon which the cervical neck orthotic device 400 is placed. In certain examples, a lower portion of the base can be removed to lower the height of the apex or a lower portion of the base can be added to raise the height of the apex. In certain examples where the base 401 includes multiple portions, each removable portion of the base can include a first major surface and a second major surface, a portion of each lateral sidewall 402, 412 and a portion of each longitudinal sidewall 403, 413. In certain examples, the removable portions of the base 401 can include an attachment entity to allow secure attachment and easy removal of the removeable portions from the cervical neck orthotic device 401. Such attachment entities can include, but are not limited to, a portion of a zipper, a portion of a hook and loop device, a portion of a snap fastener, a portion of a button fastener, glue, adhesive tape, or combinations thereof.

Figure 5:
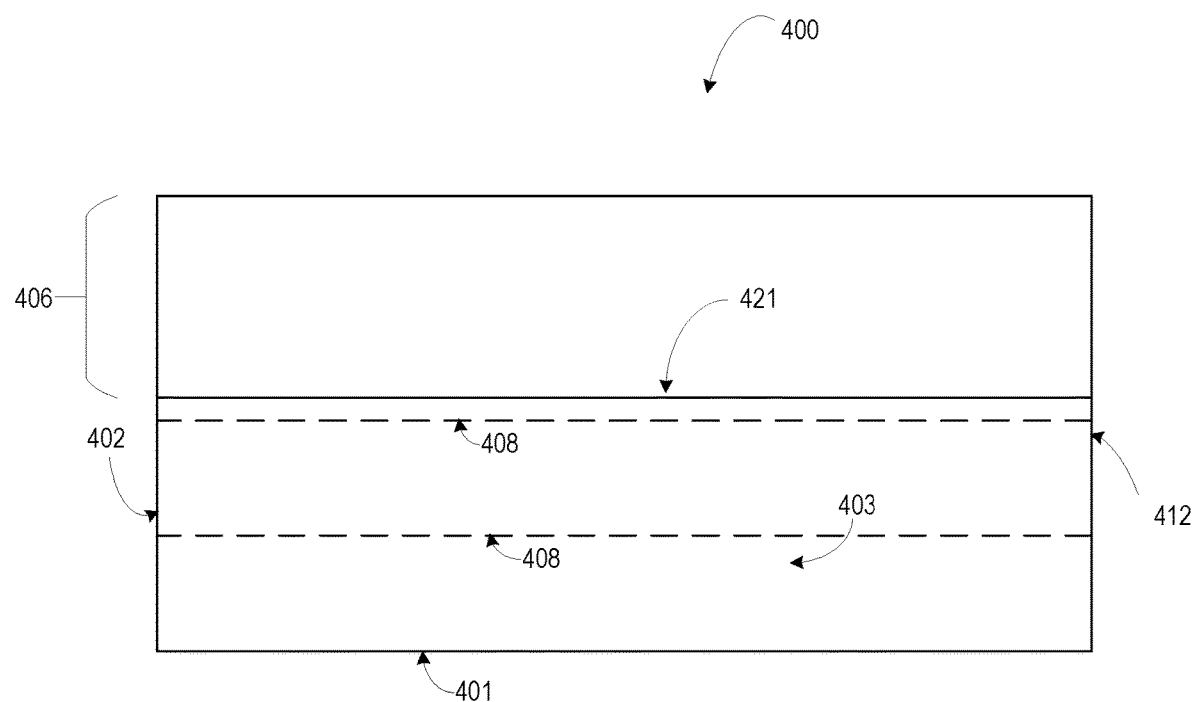
FIG. 5 is an elevation view of a minor side of the improved cervical orthotic device of FIG. 4.

FIG. 5 illustrates generally an elevation view including the first longitudinal sidewall 403. The view can illustrate the locations of the channel 415, a portion of the cervical support surface 404 including the first planar cervical support surface 406, a first end wall or first lateral sidewall 402, and the second end wall or second lateral sidewall 412. FIG. 5 also shows lines 408 defined by optional, separable portions of the base 401.

Figure 6:
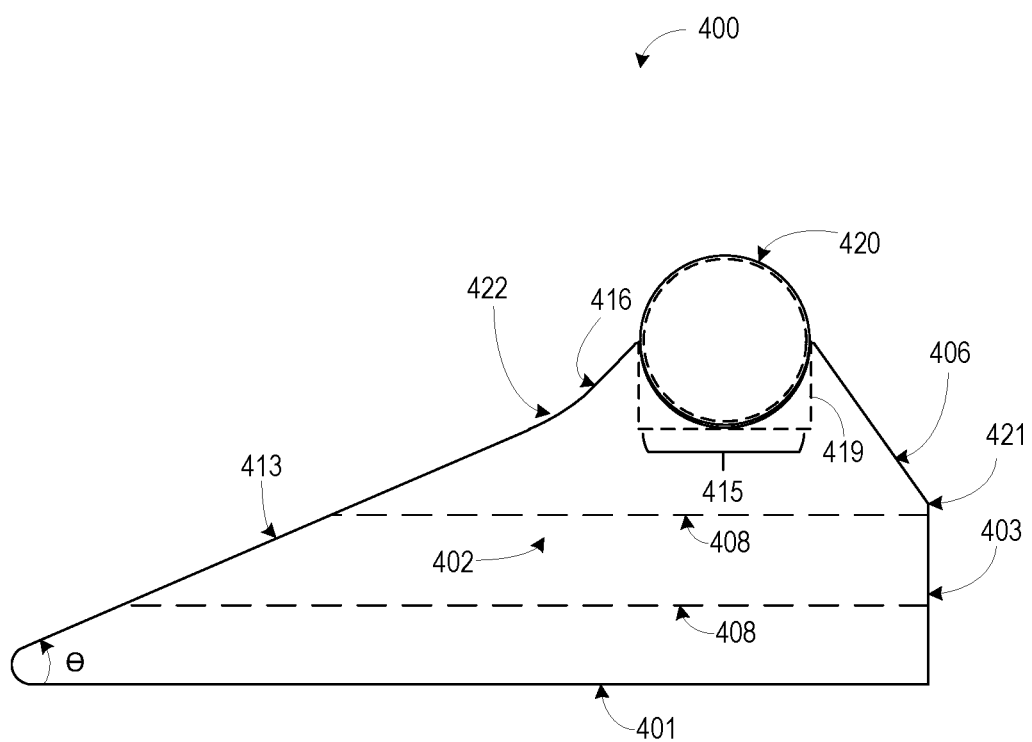
FIG. 6 is an elevation view of a major side of the improved cervical orthotic device of FIG. 4.

FIG. 6 illustrates generally an elevation view of a major side of the cervical orthotic device 400 including the first lateral sidewall 402, or first end wall, of the cervical orthotic device 400. The view can illustrate the location of a first longitudinal sidewall 403, the second longitudinal sidewall 413, the planar cervical support portions 406, 416, the channel 415, a corresponding enhancement device 420 within the channel 415, and optional square-shaped channel 419, and the base 401. FIG. 6 also shows lines 408 defined by and associated with optional removable portions of the base 401. In certain examples, the channel sidewalls can define a height of the cervical orthotic device 401 as measured from a lower surface of the base 101 whether the base includes one or more removeable portions or not. In general, the height of the cervical orthotic device 401 can range from about 2 in. to about 6 in. In some examples, each removable portion of the base can vary between about 0.75 in. and 1.25 in.

In general, the line defined by where the first longitudinal sidewall 403 meets the lower surface of the base 401 can define a width of the cervical orthotic device 400. In certain examples, the width of the cervical orthotic device 400 can range from about 3.5 in. to about 4.5 in. In some examples, a nominal width of the cervical orthotic device is about 4 in. In general, the line defined by where one of the lateral sidewalls 402, 412 meets the lower surface of the base 401 can define a length of the cervical orthotic device 400. In certain examples, the length of the cervical orthotic device 100 can range from about 6 in. to about 18 in. In certain examples, the length of the cervical orthotic device 100 can range from about 9 in. to about 12 in. In some examples, a nominal width of the cervical orthotic device is about 10.25 in.

In certain examples, the enhancement device 420 can include, but is not limited to, a firm positioning device or a cushion, a heat pack, a cold pack, a microwaveable heat pack, a gel pack, a combination hot/cold pack, a moist heat therapy pack or combinations thereof. As such, the example cervical orthotic device 400 can provide a combination of rotational cervical traction and thermal therapy to a user. In certain examples, the cervical orthotic device of each FIG. 1 or FIG. 4 can include closed cell cross-linked polyethylene (XLPE) foam. XLPE foam can provide resiliency, desired cushioning, and a smooth, soft aesthetic feel, which can be desirable characteristics for a user of a cervical orthotic device according to the present disclosure.

ADDITIONAL EXAMPLES AND NOTES

Example 1 is a cervical orthotic device comprising: a base; sidewalls extending upwardly from the base; a cervical support surface opposite the base and configured to unite the sidewalls; wherein the sidewalls include, opposingly paired lateral sidewalls and first and second longitudinal sidewalls; and wherein the cervical support surface can include a first planar portion adjacent the first longitudinal sidewall, a second planar portion adjacent the second longitudinal sidewall, and an arcuate portion intermediate the first and second planar portions.

In Example 2, the subject matter of Example 1 includes, wherein the arcuate portion is a ridge extending between, and perpendicular to, the opposingly paired lateral sidewalls, the ridge configured to engage a posterior portion of a cervical spine of a user.

In Example 3, the subject matter of Examples 1-2 includes, wherein the arcuate portion does not include a channel.

In Example 4, the subject matter of Examples 1-3 includes, wherein the cervical orthotic device is configured to engage a posterior portion of a neck of a user; and wherein the cervical orthotic device is not configured to support an anterior portion of a head of the user when the posterior portion of the neck is engaged with the cervical orthotic device.

In Example 5, the subject matter of Examples 1-4 includes, wherein the arcuate portion forms a channel extending between, and perpendicular to, the opposingly paired lateral sidewalls.

In Example 6, the subject matter of Example 5 includes, wherein the arcuate portion does not include a ridge configured to engage a cervical spine of a user.

In Example 7, the subject matter of Examples 5-6 includes, wherein the cervical orthotic device is configured to support a weight of a user's head indirectly and only via a separate device positioned in the channel.

In Example 8, the subject matter of Examples 1-7 includes, wherein the first longitudinal sidewall extends perpendicular the base to meet the first planar portion.

In Example 9, the subject matter of Examples 1-8 includes, wherein the second longitudinal sidewall extends at an acute angle from the base to meet the second planar portion.

In Example 10, the subject matter of Examples 1-9 includes, wherein the first longitudinal sidewall meets the first planar portion of the arcuate portion at a first node line; wherein the second longitudinal sidewall meets the second planar portion of the arcuate portion at a second node line; and wherein the first node line is located closer to the base than the second node line.

Example 11 is a system comprising: an enhancement device configured to engage a cervical spine of a user; and a cervical orthotic device including a channel to support the enhancement device.

In Example 12, the subject matter of Example 11 includes, wherein the enhancement device is configured to form a ridge when supported by the channel; and wherein the ridge is configured to engage a posterior portion of a neck of the user.

In Example 13, the subject matter of Example 12 includes, wherein the cervical orthotic device is configured to support a weight of a head of the user only at the ridge.

In Example 14, the subject matter of Examples 11-13 includes, wherein the cervical orthotic device includes: a base; sidewalls extending upwardly from the base; a cervical support surface opposite the base and configured to unite the sidewalls; wherein the sidewalls include opposingly paired lateral sidewalls and first and second longitudinal sidewalls; and wherein the cervical support surface can include a first planar portion adjacent the first longitudinal sidewall, a second planar portion adjacent the second longitudinal sidewall, and an arcuate portion intermediate the first and second planar portions.

In Example 15, the subject matter of Example 14 includes, wherein the arcuate portion defines the channel.

In Example 16, the subject matter of Examples 14-15 includes, wherein the first longitudinal sidewall extends perpendicular the base to meet the first planar portion.

In Example 17, the subject matter of Examples 14-16 includes, wherein the second longitudinal sidewall extends at an acute angle from the base to meet the second planar portion.

In Example 18, the subject matter of Examples 14-17 includes, wherein the enhancement device includes a heat/cold pack cushion.

In Example 19, the subject matter of Examples 14-18 includes, wherein the enhancement device includes moist heat cushion.

In Example 20, the subject matter of Examples 14-19 includes, wherein the enhancement device is a microwaveable cushion configured to provide moist heat therapy to the user.

Example 21 is an apparatus comprising means to implement of any of Examples 1-20.

Example 22 is a system to implement of any of Examples 1-20.

Example 23 is a method to implement of any of Examples 1-20.

Each of these non-limiting examples can stand on its own, or can be combined with one or more of the other examples in any permutation or combination. The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, the terms "including" and "comprising" are open-ended, that is, a system, device, article, composition, formulation, or process that includes elements in addition to those listed after such a term in a claim are still deemed to fall within the scope of that claim. Moreover, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of any claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. The following aspects are hereby incorporated into the Detailed Description, with each aspect standing on its own as a separate embodiment, and it is contemplated that such embodiments can be combined with each other in various combinations or permutations.

What is claimed is:

1. A cervical orthotic traction device comprising:
a base having a length and a width, wherein the length is longer than the width;
sidewalls extending upwardly from the base;
a cervical support surface opposite the base and configured to unite the sidewalls;
wherein the sidewalls include opposingly paired lateral sidewalls and first and second longitudinal sidewalls;
wherein the cervical support surface includes a first planar portion adjacent the first longitudinal sidewall, a second planar portion adjacent the second longitudinal sidewall, and an arcuate portion intermediate the first and second planar portions and extending between, and perpendicular to, the opposingly paired lateral sidewalls;
wherein the first longitudinal sidewall meets the first planar portion of the arcuate portion at a first node line and the second longitudinal sidewall meets the second planar portion of the arcuate portion at a second node line;

wherein the second longitudinal sidewall extends at an acute angle from the base to meet the second planar portion at the second node line, wherein the second planar portion extends from the second node line at a greater angle with respect to the base than the acute angle of the second longitudinal sidewall from the base; and wherein the arcuate portion of the cervical support surface is configured to support cervical vertebrae of a user to allow a weight of a head of the user to assist with rotational cervical traction or stretching of the cervical vertebrae or muscles.

2. The cervical orthotic device of claim 1, wherein the arcuate portion is a ridge extending between, and perpendicular to, the opposingly paired lateral sidewalls, the ridge configured to engage a posterior portion of the cervical vertebrae including at least one of C1-C7 of a cervical spine of the user.

3. The cervical orthotic device of claim 1, wherein the arcuate portion does not include a channel.

4. The cervical orthotic device of claim 1, wherein the cervical orthotic device is configured to engage a posterior portion of a neck of the user; and wherein the cervical orthotic device is not configured to support an anterior portion of the head of the user when the posterior portion of the neck is engaged with the cervical orthotic device.

5. The cervical orthotic device of claim 1, wherein the arcuate portion forms a channel extending between, and perpendicular to, the opposingly paired lateral sidewalls.

6. The cervical orthotic device of claim 5, wherein the arcuate portion does not include a ridge configured to engage a cervical spine of the user.

7. The cervical orthotic device of claim 5, wherein the cervical orthotic device is configured to support the weight of the head of the user indirectly and only via a separate device positioned in the channel.

8. The cervical orthotic device of claim 7, wherein the separate device positioned in the channel comprises an enhancement device configured to engage a cervical spine of the user.

9. The cervical orthotic device of claim 8, wherein the enhancement device is configured to form a ridge when supported by the channel; and wherein the ridge is configured to engage a posterior portion of a neck of the user.

10. The cervical orthotic device of claim 9, wherein the cervical orthotic device is configured to support the weight of the head of the user indirectly and only at the ridge.

11. The cervical orthotic device of claim 8, wherein the enhancement device includes a heat/cold pack cushion.

12. The cervical orthotic device of claim 8, wherein the enhancement device includes moist heat cushion.

13. The cervical orthotic device of claim 8, wherein the enhancement device is a microwaveable cushion configured to provide moist heat therapy to the user.

14. The cervical orthotic device of claim 1, wherein the first longitudinal sidewall extends perpendicular the base to meet the first planar portion.

15. The cervical orthotic device of claim 1, wherein the second longitudinal sidewall is longer than the second planar portion.

16. The cervical orthotic device of claim 15, wherein the acute angle of the second longitudinal sidewall and the greater angle of the second planar portion are both less than 90 degrees with respect to the base.

17. The cervical orthotic device of claim 1, wherein
the first node line is located closer to the base than the second node line.

18. The cervical orthotic device of claim 1, wherein the width of the base is between 3.5 inches and 4.5 inches to support at least a portion of the thoracic spine of the user but not a boney or muscular structure of shoulders of the user, allowing the shoulders of the user to lower with respect to the thoracic spine to allow for easier breathing during the rotational cervical traction or the stretching of the cervical vertebrae or muscles.

19. The cervical orthotic device of claim 1, wherein the length of the base is between 6 inches and 18 inches to allow the weight of the head of the user to assist with the rotational cervical traction or the stretching of the cervical vertebrae or muscles.

20. The cervical orthotic device of claim 1, wherein the base includes at least one removable portion configured to vary, by removal, a height of the cervical orthotic traction device to be between 2.5 inches and 6 inches.

* * * * *